Figure 1:
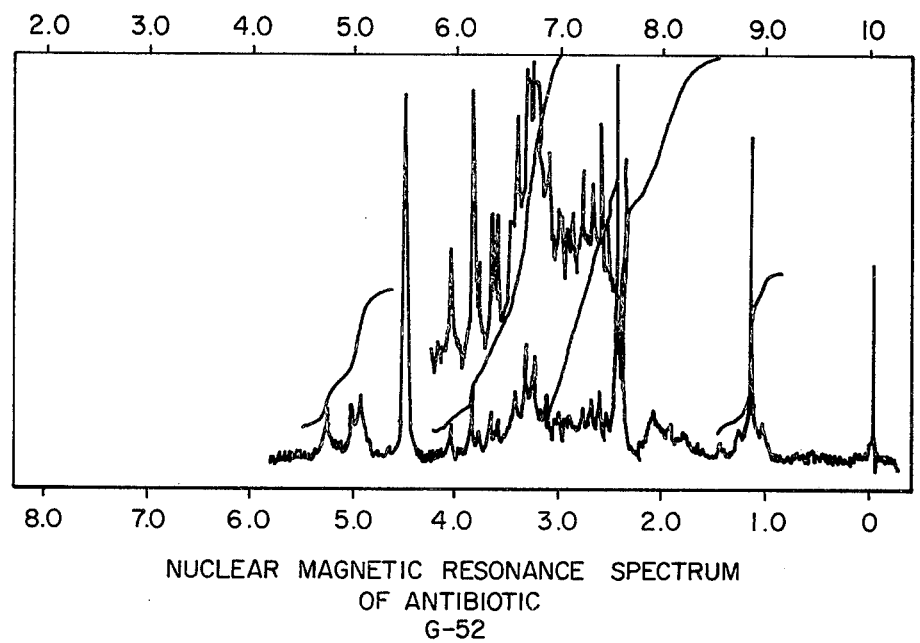

United States Patent [19]
Weinstein et al.

[11] B 4,001,209
[45] Jan. 4, 1977

[54] ANTIBIOTIC G-52 AND METHOD FOR THE PRODUCTION THEREOF

[75] Inventors: Marvin J. Weinstein; Gerald H. Wagman, both of East Brunswick; Joseph A. Marquez, Montclair, all of N.J.

[73] Assignee: Schering Corporation, Kenilworth, N.J.

[22] Filed: Feb. 28, 1975

[21] Appl. No.: 554,291

[44] Published under the second Trial Voluntary Protest Program on March 9, 1976 as document No. B 554,291.

Related U.S. Application Data

[63] Continuation-in-part of Ser. No. 271,838, July 14, 1972, abandoned.

[52] U.S. Cl. .................................. 536/17; 195/96; 424/180; 424/181

[51] Int. Cl.² ........................................ C07H 15/22
[58] Field of Search ................. 260/210 AB, 210 R

[56] References Cited

UNITED STATES PATENTS

| | | | |
|---|---|---|---|
| 3,651,042 | 3/1972 | Marquez et al. | 260/210 AB |
| 3,832,286 | 8/1974 | Weinstein et al. | 260/210 AB |

*Primary Examiner*—Johnnie R. Brown
*Attorney, Agent, or Firm*—Stephen B. Coan; Raymond A. McDonald; C. C. Joyner

[57] ABSTRACT

A novel *actinomycete* herein designated *Micromonospora zionensis* elaborates a product having substantial antibacterial activity, said activity being due to sisomicin and the novel antibiotic substance coproduced therewith. The disclosure sets forth methods for producing, isolating and using the antibiotics.

5 Claims, 2 Drawing Figures

NUCLEAR MAGNETIC RESONANCE SPECTRUM
OF ANTIBIOTIC
G-52

WAVELENGTH (MICRONS)
INFRARED SPECTRUM OF ANTIBIOTIC
G-52

ANTIBIOTIC G-52 AND METHOD FOR THE PRODUCTION THEREOF

This application is a continuation-in-part of our co-pending application Ser. No. 271,838, filed July 14, 1972 now abandoned.

This application relates to the cultivation of a novel *actinomycete* and to the novel product elaborated thereby. More particularly, this application relates to a new species of *Micromonospora* herein designated *Micromonospora zionensis* (sometimes referred to as *M. zionensis*). This application also relates to a method for producing a novel antibiotic (herein designated Antibiotic G-52) and to a new method for preparing a heretofore known antibiotic, sisomicin.

THE MICROORGANISM

*Micromonospora zionensis* described herein has been classified as a new species of Micromonospora based upon its taxonomical and growth properties on a number of standard media and upon the identifying characteristic relating to the antibiotic complex produced thereby; (i.e. the complex consisting of Antibiotic G-52, and sisomicin). Thus, this invention in its generic aspect relates to a process whereby *Micromonospora zionensis* is fermented to produce a novel antibiotic complex. The process also relates to mutants and variants of said *M. zionensis* having the identifying characteristics thereof including the elaboration of the aforementioned antibiotic complex. On such media the microorganism appears to be more closely related to *Micromonospora echinospora* than to any previously described microorganism; however, substantial differences appear when the growth characteristics of the two microorganisms are compared. These differences are particularly noticeable in the following respects:

| Medium | M. zionensis | M. echinospora |
| --- | --- | --- |
| Glucose asparagine agar | growth poor, flat, cream colored | growth fair, color—bright peach—g5IA moderate reddish orange 37 |
| Bennett's agar | color — black | color—deep maroon—g7 ½ PL; dark grayish reddish brown 47 |
| Emerson's agar | g4nl chocolate; dark grayish yellowish brown 81 | color— tile red — g5NE; strong brown 55 |
| Tomato paste oatmeal agar | black | color — dusty orange g4LC; moderate orange 53 |
| Rhamnose utilization | poor | good |

*Micromonospora zionensis* has been deposited at the Northern Utilization Research and Development Division, U.S. Department of Agriculture, Peoria, Illinois and added to its collection of microorganisms as NRRL 5466.

The microorganism has the microscopic, macroscopic and biochemical properties set forth below.

1. Taxonomy a. Macroscopic observations of 30 day old culture incubated at 24°–26°C on a 3% NZ Amine Type A, 1% dextrose and 1.5% agar medium shows fair growth with no aerial mycelium, no diffusible pigment, g3cc bisque, light grayish yellowish brown 79.

b. Microscopic observations of the organism after 60 days incubation on yeast extract-sucrose medium shows abundant spores which are globose to spherical in shape, are about 1.0 – 1.5 μm in diameter and are produced on short sporophores.

In the preceding and the following descriptions of the microorganisms two color designates are used. The first is taken from the "Color Harmony Manual", 4th Edition 1958, published by the Container Corporation of America (U.S.A.) and the description for the first designate is taken from the "Descriptive Color Name Dictionary" by Taylor, Knoche and Granville also published by the Container Corporation of America (1950). The second color designate is a synonym or near synonym of the first and is taken from the National Bureau of Standards Circular No. 553 (1955) U.S.A.

CULTURAL CHARACTERISTICS

1. *Micromonospora zionensis* generally shows good growth at 28° to 37°C and substantially no growth at 45°C or above. The microorganism is aerobic and grows at a pH range of about 6.5 to 8.3, however, it grows and produces best at a pH approaching neutrality.

2. The microorganism exhibits substantially no growth on the following standard media: glucose-Czapek's, glucose-asparagine, calcium malate, ordinary agar (water agar), nutrient agar, egg agar (Dorset Egg Medium), gelatin, starch and cellulose.

3. Potato Plug - growth: poor, light reddish brown, when calcium carbonate is added to the potato plug, growth is good, plicate, black.

4. Loffler's Serum - growth: fair, cream colored, substrate reduced to a liquid.

5. Peptone - glucose agar - growth: fair, membranous, no aerial mycelium, no diffusible pigment, g3ic light amber; dark orange yellow 72.

6. Litmus milk - peptonized giving acid reaction.

7. Tyrosine medium - growth: poor - does not produce tyrosinase.

8. Carbohydrate utilization: the microorganism exhibits good growth on D-arabinose, L-arabinose, D-galactose, D-glucose, mannose, sucrose, D-xylose and starch; fair growth is exhibited on D-lactose, D-levulose and D-ribose; poor growth is exhibited on dulcitol, glycerol, L-inositol, D-mannitol, melibiose, melizitose, raffinose, L-rhamnose, sorbitol and salicin. Cellulose is decomposed very slowly. The control medium contains 0.5% yeast extract and no added carbohydrate. The microorganism exhibits poor growth on this medium, therefore, any enhancement in the growth characteristics of the microorganism is due to the utilization of the 1% added carbohydrate.

9. Nitrogen Utilization - These data are obtained with media containing a single added nitrogen source plus 1% glucose w/v.

a. 0.5% Yeast extract (Difco) growth: good, membranous, no aerial mycelium, no diffusible pigment, g4ng light brown; strong brown 55;

b. 1.0% NZ Amine - type A (Sheffield Chem. Co., Norwich, New York) - growth: fair, flat, no aerial mycelium, no diffusible pigment, g3ca pearl pink; pale orange yellow 73.

c. 1.0% Asparagine - growth: poor, flat, no aerial mycelium, no diffusible pigment, g6ng brick red; moderate reddish brown 43.

d. 1.0% Glutamic acid - growth and color characteristics are the same as in item (c).

e. 1.0% Sodium nitrate - no visible growth.

f. 1.0% Ammonium nitrate - no visible growth.

10. Salt tolerance - The microorganism will tolerate a maximum of 3% sodium chloride in a growth medium.

11. Bennett's Agar - growth: good, plicate - membranous, no aerial mycelium, no diffusible pigment, black.

12. Emerson's Agar - growth: fair, plicate, no aerial mycelium, no diffusible pigment, black.

13. Glucose - yeast extract agar - growth; good, plicate, no aerial mycelium, no diffusible pigment, g6ni taupe brown; grayish reddish brown 46.

14. Czapek's Agar - growth: poor.

15. Tyrosine Agar - growth: very poor on tyrosine beef extract agar - does not produce tyrosinase growth: fair on tyrosine yeast extract agar; tyrosinase produced (crystals dissolved), light brown diffusible pigment. Observations at 2, 7 and 14 days - (see Gordon and Smith J. Bact. 69:147.)

16. Peptone Iron Agar - growth: good, no hydrogen sulfide produced.

17. Brain Heart Infusion Agar - growth: fair, plicate, membranous, no aerial mycelium, no diffusible pigment g3Le, yellow maple; strong yellowish brown 74.

18. Malt Extract Agar A - growth: good, plicate, membranous, no aerial mycelium, no diffusible pigment, g5pg rust brown; strong brown 55.

19. Malt Extract Agar B - growth: good, membranous, no aerial mycelium, no diffusible pigment, g4Lg light spice brown; moderate brown 58.

The foregoing cultural characteristics serve to distinguish *Micromonospora zionensis* from all previously described microorganisms. In addition to the foregoing, *Micromonospora zionensis* may also be distinguished by its production under aerobic fermentation conditions of a novel composition of matter, namely a complex of Antibiotic G-52 and sisomicin.

PRODUCTION OF ANTIBIOTIC G-52

*Micromonospora zionensis* produces Antibiotic G-52 when cultivated in a nutrient medium containing assimilable sources of carbon and nitrogen. Substantial quantities of the antibiotic are produced when the microorganism is cultivated in an aqueous nutrient medium under submerged aerobic conditions. Exemplary of assimilable carbon sources are carbohydrates, such as, those set forth hereinabove, especially glucose, xylose, and sucrose. Exemplary of assimilable sources of nitrogen are proteins, amino acids and substances containing the same such as, beef extract, yeast extract, soybean meal, and the like. Specific examples of such nitrogen sources are set forth hereinabove under the heading Nitrogen Utilization. Good growth and antibiotic production may be obtained using the fermentation media and procedures set forth in the specific examples The media may be supplemented with trace amounts of inorganic salts such as magnesium sulfate, ferrous sulfate, and especially, cobalt chloride to enhance antibiotic production. In general, the fermentation is conducted at a temperature range of from about 23°C to about 38°C with continuous aeration and continuous agitation at from about 250–400 rpm. Under these conditions, peak antibiotic production is attained in from about 2 to about 4 days. The pH of the fermentation is generally maintained in the range of from about 6.5 to about 8.3, preferably about 7.2. In small scale fermentations, e.g. 10 liters, it is usually not necessary to adjust the pH of the fermentation after inoculation. In large scale fermentations, however, it may be necessary to add materials to raise or lower the pH of the medium. These materials are those generally used in the art, e.g. dilute mineral acids, dilute alkali and alkaline earth metal hydroxides and carbonates and the like.

Generally, the fermentation is carried out in two or more stages, there being one or more germination stages followed by a fermentation stage. As a general rule, large (tank) fermentations utilize two germination stages whereas shake flask fermentations utilize a single germination stage.

During the course of the fermentation especially after the first 24 hours, the fermentation is assayed at convenient intervals (e.g. every 6 to 8 hours), to determine when peak production is reached.

Microbiological Assay

The assay is a standard disc plate assay using Difco Antibiotic Medium No. 5 and *Staphylococcus aureus* A.T.C.C. 6538P as the test organism. The physical conditions of the test are substantially those described for neomycin [Grove and Randall, Assay Methods of Antibiotics published by Medical Encyclopedia Incorporated (1955)]. The assay is run against a standard preparation of Antibiotic G-52 having a defined potency of 1000 mcg/mg. One microgram of the standard gives a zone of inhibition of 17.7 ± 1.0 mm in the test. The standard antibiotic sulfate salt assays about 675 mcg/mg. against the standard antibiotic base.

When peak antibiotic activity is attained, the product is harvested, generally, by a combination of steps known in the art, such as, acidification, filtration, adsorption, elution, lyophilization and the like. In a preferred isolation (harvesting) procedure, the whole broth is acidified preferably with a mineral acid and the fermentation mixture clarified by filtration or centrifugation. After neutralization, the antibiotic product is adsorbed upon a suitable cation exchange resin, such as, Amberlite IRC-50 (Rohm and Haas, Philadelphia, Pennsylvania), eluted with dilute alkali, preferably ammonium hydroxide and isolated by lyophilization.

The product obtained by the foregoing procedure contains the entire compliment of antibiotics produced by the fermentation.

The antibiotic complex is separated by subjecting the crude lyophilizate to chromatography on a solid adsorbent such as alumina, cellulose, diatomaceous earth, magnesium silicate or preferably silica gel. Elution may be effected by known methods with any suitable polar organic solvent or solvent mixture. However, when silica gel is employed as the solid adsorbent, elution is advantageously effected by the use of the lower phase of a solvent mixture consisting of chloroform, isopropanol and concentrated ammonium hydroxide (2:1:1 v/v). In this manner, the antibiotic complex is separated into the two major components, there being evidence of traces of as yet unidentified active materials. The first antibiotic eluted from the column is Antibiotic G-52, followed by sisomicin.

THE ANTIBIOTICS

Sisomicin, the heretofore known antibiotic produced by the above-described process is also known as Antibiotic 66-40 and as rickamicin. Its gross structure is shown on page 285 of Chemical Communications, 1971, the Chemical Society, Burlington House, London. The fermentation, isolation and biological properties of sisomicin are described in the U.S. Pat. No. 3,832,286 issued Aug. 27, 1974.

Antibiotic G-52 and its pharmaceutically acceptable derivatives adversely affect the growth of gram-positive and gram-negative microorganisms. Further, Antibiotic G-52 and its pharmaceutically acceptable derivatives may be utilized under in vivo or under in vitro conditions to eradicate or inhibit susceptible bacteria. The antibiotic and its derivatives may be used in conjunction with soaps and detergents to destroy and remove such organisms from the surface of laboratory equipment, surgical instruments, laboratory glassware, and the like. The antibiotic and its pharmaceutically acceptable derivatives, may also be used to destroy or substantially inhibit susceptible organisms within mammalian hosts, such as mice, rats, cats, dogs, cattle and the like.

As used herein the term pharmaceutically acceptable derivatives embraces acid addition salts and Schiff baseoxazolidine derivatives of Antibiotic G-52 or their equivalents.

PHYSICOCHEMICAL PROPERTIES OF ANTIBIOTIC G-52

General

Antibiotic G-52 is a white solid which is very soluble in water and has some degree of solubility in most polar organic solvents such as lower alcohols, di-loweralkyl acylamides (e.g. dimethylformamide) di-loweralkylsulfoxides (e.g. dimethylsulfoxide), pyridine and the like.

Further, the antibiotic is stable to boiling for at least thirty (30) minutes in MacIlvaines buffer from pH 2–8 and in sodium hydroxide-boric acid buffer from pH 8–10. The antibiotic exhibits no absorption in the ultraviolet in the range of 220–400 m$\mu$.

Antibiotic G-52 has a characteristic NMR spectrum as shown by FIG. 1. The spectrum was obtained by the use of a Varian A-60-A spectrometer (Varian Associates, 611 Hansen Way, Palo Alto, California) on a solution of the antibiotic in deuterated water ($D_2O$). For structure determination, the following absorption peaks are considered relevant: ($\Delta$, PPM) 1.20 singlet, 1.20 multiplet, 2.43 singlet, 2.50 singlet, 3.80 quartet, 4.02 doublet, 5.03 broad singlet, 5.07 doublet and 5.35 doublet.

Figure 2:
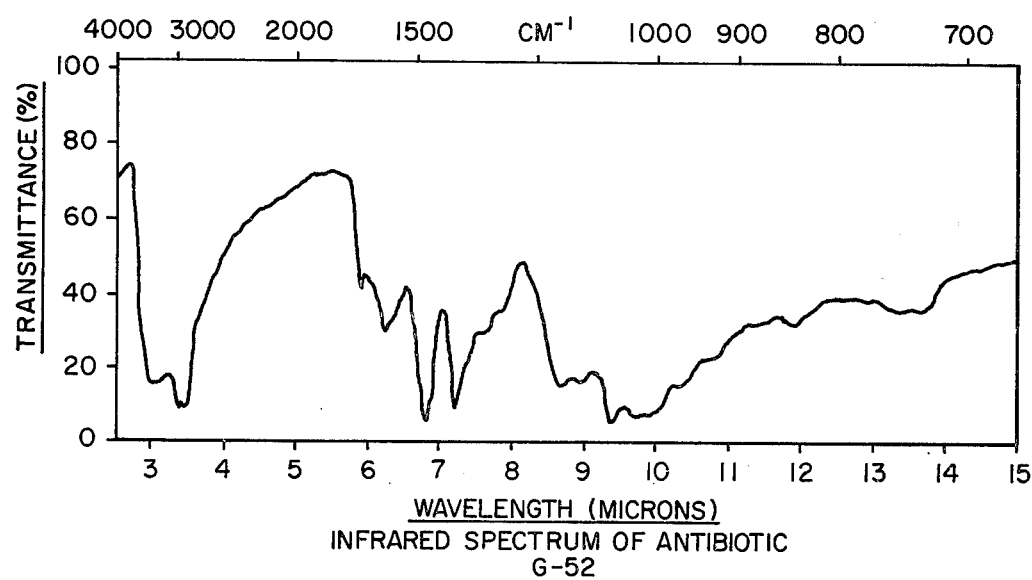

The antibiotic has a characteristic infrared absorption spectrum as shown by FIG. 2.

The mass spectrum of Antibiotic G-52 shows a molecular ion at 461 which is confirmed by other fragmentations in the spectrum and is in good agreement with an empirical formula of $C_{20}H_{39}N_5O_9$.

The physicochemical data set forth herein, especially the NMR, infrared and the mass spectra are consistent with the following planar (flat) structure for Antibiotic G-52. However, no conclusions relative to its stereochemistry are to be drawn therefrom:

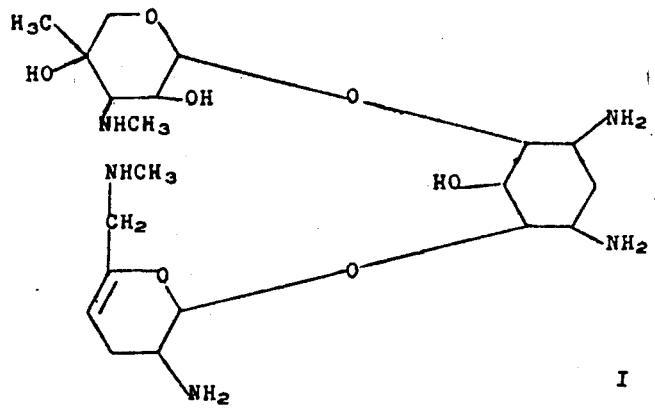

I

Antibiotic G-52 may also be depicted stereochemically as set forth in Formula Ia below:

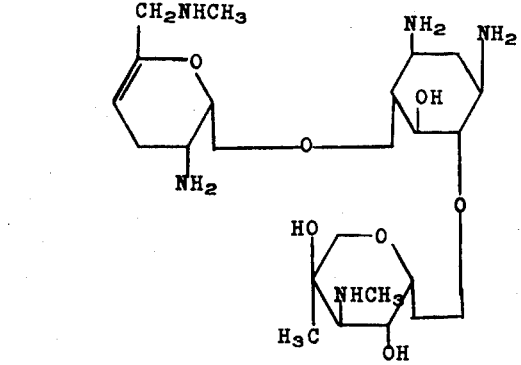

Antibiotic G-52 is an aminoglycoside antibiotic and therefore belongs to the class that includes gentamicin, neomycin, paromomicin, tobramycin, sisomicin, kanamycin and the like. It is a basic compound which forms non-toxic acid addition salts with acids; such as hydrochloric, sulfuric, phosphoric, acetic, propionic, maleic, tartaric, benzoic, stearic, pimelic, cyclopropane carboxylic, adamantane carboxylic acids and the like. The salts derived from Antibiotic G-52 and such acids are soluble in water and exhibit the same antibacterial properties as does the antibiotic free nitrogen base. Thus, these salts may be used in the same manner and for the same purposes described above.

It is of value to note that Antibiotic G-52 and its acid addition salts like many other aminoglycoside antibiotics form hydrates and solvates which may be difficult to break. Consequently, for the most part, they may be utilized in the solvated or hydrated form with a suitable adjustment for antibiotic content.

Chromatographic comparisons of Antibiotic G-52 with other representative amino-glycoside antibiotics are set forth in Table 1 below.

TABLE 1

| Paper Chromatographic Systems | Comparative $R_f$ Values $R_f$'s of Antibiotics | | | | | | | |
|---|---|---|---|---|---|---|---|---|
| | Antibiotic G-52 | Sisomicin | $C_1$ | Gentamicin Components $C_2$ | $C_{1a}$ | Neomycin | Kanamycin | Paromomycin |
| 80% methanol plus 3% sodium chloride (W/V) 1:1 descending[a] | 0.55 | 0.45 | 0.57 | 0.56 | 0.48 | 0.0, 0.17 | 0.0, 0.28 | 0.0, 0.28 |
| Propanol:pyridine: acetic acid:water (6:4:1:3) ascending (V/V) | 0.29 | 0.22 | 0.34 | 0.30 | 0.22 | 0.05 | 0.08 | 0.07 |
| 80% phenol ascending (V/V) | 0.45 | 0.45 | 0.45 | 0.45 | 0.45 [v] | 0.0, 0.12 | 0.0, 0.17 | 0.0, 0.2 |
| Benzene:methanol (V/V) 9:1 descending | 0.0 | 0.0 | 0.0 | 0.0 | 0.0 | 0.0 | 0.0 | 0.0 |
| N-butanol:water: acetic acid (4:5:1) upper phase used ascending | 0.0 | 0.0 | 0.0 | 0.0 | 0.0 | 0.0 | 0.0 | 0.0 |

[a]Paper buffered with 0.95 molar $Na_2SO_4$ + 0.05 molar $NaHSO_4$

| Paper Chromatographic Systems | Antibiotic G-52 | Sisomicin | $C_1$ | Gentamicin Components $C_2$ | $C_{1a}$ |
|---|---|---|---|---|---|
| Chloroform: methanol:17% ammonium hydroxide 2:1:1 | 0.48 | 0.21 | 0.67 | 0.40 | 0.21 |

$R_f$'s of Antibiotics, t = 16 hours

| | Antibiotic G-52 | Sisomicin | Gentamicin Components $C_2$ | $C_{1a}$ |
|---|---|---|---|---|
| 2 Butanone:tert-butanol:methanol: conc. ammonium hydroxide 16:3:1:6 | 0.73 | 0.59 | 0.75 | 0.65 |

$$Rt = \frac{\text{distance of zone from origin}}{\text{distance from origin to end of paper}} \text{ at time } t$$

Similarly, the pharmaceutically acceptable Schiff base-oxazolidine derivatives of Antibiotic G-52 are generally prepared by treating an alcoholic solution of the antibiotic free nitrogen base with an excess of aldehyde above ambient temperature, preferably at reflux for about 1 hour and chilling the solution to obtain the desired product, usually in the form of a crystalline solid. As can be seen from Formula I above, the antibiotic has three primary amino groups, each of which can form a Schiff base. Further, the antibiotic has a secondary amino group vicinal to a tertiary hydroxy group which combination with aldehyde, gives rise to an oxazolidine ring. Thus, when the antibiotic is reacted with an excess of aldehyde, four moles of aldehyde react with each mole of antibiotic to yield a Schiff base-oxazolidine derivative. These derivatives are also useful for the same purposes described above. However, due to their solubility properties, they are most useful when employed in oleaginous media, such as creams, jellys or ointments. The Schiff base-oxazolidines are not appreciably water soluble and are in fact decomposed in aqueous media containing traces of acid. Conversely, they are soluble in most commonly used non-acidic organic solvents.

BIOLOGICAL PROPERTIES OF ANTIBIOTIC G-52

In vitro Antibacterial Activity

Minimum Inhibitory Concentration

| Organism | MIC (mcg/ml) |
|---|---|
| Staphylococcus aureus 209P | 0.3 |
| Staphylococcus aureus 45 | 0.8 |
| Streptococcus pyogenes C | 25 |
| Escherichia coli 11775 | 3.0 |
| Escherichia coli 578 | 7.5 |
| Klebsiella pneumoniae Ad 17 - kR | 0.8 |
| Proteus mirabilis 8019 | 7.5 |
| Pseudomonas aeruginosa 236 - GR | 25 |
| Pseudomonas aeruginosa 130 - GR | 25 |
| Salmonella paratyphi 13311 | 17.5 |

Test Medium: Tryptose phosphate broth at pH 7.2.

In vivo Activity of Antibiotic G-52 in Mice

Protective Activity[a]

| Organism | Treatment Route | $PD_{50}$ (mg/kg) |
|---|---|---|
| Staphylococcus aureus Gray | S.C. | 2.5 |
| Escherichia coli | S.C. | 2.5 |
| Pseudomonas aeruginosa | S.C. | 1.5 |

| Organism | Treatment Route | PD$_{50}$ (mg/kg) |
|---|---|---|

| Route | Acute Toxicity[b] LD$_{50}$ (mg/kg) |
|---|---|
| I.V. | 50 |
| S.C. | 400 |
| I.P. | 200 | a. Mice (Carworth Farms CF-1 weighing about 18 – 20 grams) are treated with a single dose of antibiotic (sulfate) one (1) hour after an intraperitoneal infection with a lethal ($10^7$ organisms) quantity of the infectious organism. The number of survivors are determined 48 hours after infection and the data analyzed by standard probit procedures to determine the PD$_{50}$ values with 95% confidence limits.

b. The acute toxicity of Antibiotic G-52 in the form of the sulfate salt is determined in the standard manner by administration of the antibiotic to mice (CF-1) intravenously, subcutaneously and intraperitoneally. The results are analyzed by standard probit procedures to determine the LD$_{50}$ values with 95% confidence limits.

The appended examples set forth the best mode for carrying out this invention.

EXAMPLE 1

Tank Fermentation of Micromonospora Zionensis

A. Germination Stage:
Inoculate a series of 300 ml. flasks each containing 100 ml. of sterile medium (see Medium A below) using a loopful of M. zionensis from an agar slant. Incubate the flasks with continuous agitation for from about 2 to about 4 days until vigorous growth is obtained. The incubation is preferably conducted with continuous rotary agitation at about 250 to 300 rpm at about 35°C.

B. Second Germination Stage:
Transfer 25 ml. of the inoculum prepared in step A to a series of 2 liter Erlenmeyer flasks containing 500 ml. of sterile Medium A. Incubate this medium with rotary agitation as described in step A, preferably at 28°C, until vigorous growth is obtained.

C. Fermentation Stage:
Transfer 500 ml. of the germinated culture to each of a series of 14 liter fermentors containing 10 liters of fermentation Medium (see Medium B below) and ferment the mixture with agitation at from about 200 to about 500 rpm, preferably about 400 rpm, at a temperature in the range of 26°C to 38°C preferably at 35°C, and with aeration at about 3 to 5 liters/minute. Assay the media at convenient intervals after the first 24 hours, continue the the fermentation until peak antibiotic activity is attained and harvest the antibiotic mixture as described in Example 2.

| Medium A | |
|---|---|
| Sucrose | 25 grams |
| Corn steep liquor (spray dried) | 5 grams |
| Yeast extract | 5 grams |
| N–Z amine (Sheffield Chemical Company) | 5 grams |
| Calcium carbonate | 5 grams |
| Tap water | 1000 ml. |

| Medium B | |
|---|---|
| Soybean meal | 30 grams |
| Potato dextrin | 500 grams |
| Dextrose | 5 grams |
| Edamin (Sheffield Chemical Company) | 5 grams |
| Calcium carbonate | 7 grams |
| Ferrous sulfate | $10^{-3}$ moles/l. |

| -continued Medium A | |
|---|---|
| Cobalt chloride | $10^{-6}$ moles/l. |
| Tap water | 1000 ml. |

EXAMPLE 2

Isolation of the Antibiotic Complex

Add 380 g. of oxalic acid to 60 liters of fermentation broth and adjust to pH 2 with 6N sulfuric acid. Stir the mixture for about 20 minutes and filter, wash the mycelial cake with water and combine the clear filtrate with the mycelial washings. Adjust the pH to 7 with 6N ammonium hydroxide. Charge the filtrate with stirring to an Amberlite IRC-50 cationic exchange resin in the ammonium form, resin quantity 600–700 g. Filter to remove the resin. Wash the resin with water and elute with 2N ammonium hydroxide. Concentrate the eluate to about 100 ml. and lyophilize to obtain the antibiotic complex.

Paper chromatography of this material in the chloroform: methanol: 17% ammonium hydroxide (2:1:1 v/v) system reveals it to consist substantially of sisomicin and Antibiotic G-52 assaying 300 mcg/mg.

EXAMPLE 3

Separation of the Antibiotic Complex

Suspend 1000 g. of silica gel in the lower phase of a solvent system composed of chloroform: isopropanol: concentrated ammonium hydroxide (2:1:1 v/v) and stir into a glass column having an outer diameter of about 5 cm. The height of the settled silica gel is about 100 cm. Dissolve 12.4 g. of the antibiotic complex, prepared as described in Example 2, in water and slurry with about 100 g. of silica gel. Charge the resin containing the antibiotic complex to the top of the column. Pass the lower phase of the above-described solvent system through the column at the rate of about 1 ml. per minute and collect 10 ml. fractions.

Chromatograph an aliquot of each fraction (in duplicate) in the following solvent system; chloroform: methanol: 17% ammonium hydroxide (2:1:1 v/v). The desired material is usually located between fractions 600 to 790. The chromatogram is sprayed with ninhydrin reagent to confirm the location of ninhydrin positive fractions. The second (duplicate) chromatogram is bioautographed on an agar plate seeded with Staphylococcus aureus A.T.C.C. 6538P to confirm that the ninhydrin positive fractions are biologically active.

Combine the appropriate fractions, concentrate and lyophilize to obtain Antibiotic G-52 and sisomicin, the less polar (first to emerge) being Antibiotic G-52.

EXAMPLE 4

Preparation of Antibiotic G-52 Sulfate

Dissolve 800 mg. of Antibiotic G-52 in 100 ml. of water and adjust the pH to 4.2 with sulfuric acid. Stir the solution with activated charcoal, preferably Darco G-60 (Atlas Powder Company, Wilmington, Delaware), for about 1 hour and filter. Concentrate the filtrate and add to an excess (10 volumes) of methanol. Filter the resulting precipitate to obtain about 1.0 g. of the title product assaying 660 mcg/mg.

In a similar manner, by substituting an equivalent quantity of other acids, such as, hydrochloric, phosphoric, hydrobromic, acetic, propionic, pimelic, stearic, benzoic, tartaric, maleic, cyclopropane carboxylic or adamantane carboxylic acids; and by following the process described in Example 4 acid addition salts of such acids and Antibiotic G-52 may be formed.

EXAMPLE 5

Preparation of Antibiotic G-52 Base

Dissolve an 800 mg. portion of Antibiotic G-52 sulfate, prepared as described in Example 4, in about 10 ml. of water and charge to an Amberlite anion exchange resin column IRA-401S (OH) having the following dimensions: height, 25 cm; outside diameter, 2 cm. Elute the column with water, concentrate the eluate to about 10 ml. and lyophilize to obtain about 487 mg. of the title product having a potency of about 1000 mcg/mg.

Antibiotic G-52 may be applied topically in the form of ointments, both hydrophilic and hydrophobic, in the form of lotions which may be aqueous, non-aqueous or of the emulsion type or in the form of creams. Pharmaceutical carriers useful in the preparation of such formulations will include, for example, such substances as water, oils, greases, polyesters, polyols and the like. The Schiff base-oxazolidine derivatives are of particular advantage for preparing non-aqueous topical formulations since such derivatives exhibit compatibility with the pharmaceutical carriers generally used in such preparations.

In general, the topical preparations will contain from about 0.1 to about 3.0 gms. of antibiotic per 100 gms. of ointment, cream or lotion. The topical preparations are usually applied gently to lesions from about 2 to about 5 times a day.

Antibiotic G-52 and the above-described derivatives thereof may also be administered orally in the form of capsules, tablets, and elixirs. When so administered, they are especially effective in the treatment of diarrheas caused by gastrointestinal infection by susceptible microorganisms.

The antibiotic of this invention may be utilized in liquid form such as solutions, suspensions and the like for otic and optic use and may also be administered parenterally via intramuscular injection. The injectable solution or suspension will usually be administered at from about 1 mg. to about 5 mgs. of antibiotic per kilogram of body weight per day divided into about 2 to about 4 doses. The precise dose, in any form, to a large extent depends on the stage and severity of the infection, the susceptibility of the infecting organism to the antibiotic and the individual characteristics of the animal species being treated.

Example 6 below sets forth the ingredients and the process for making an injectable solution.

EXAMPLE 6

Injectable Solution

|  | Per 2.0 ml. Vial | Per 50 liters |
|---|---|---|
| Antibiotic G-52 sulfate | 84.0 mgs.* | 2100.0 gms.* |
| Methylparaben, USP | 3.6 mgs. | 90.0 gms. |
| Propylparaben, USP | 0.4 mgs. | 10.0 gms. |
| Sodium bisulfite, USP | 6.4 mgs. | 160. gms. |
| Disodium Ethylenediamine tetraacetate Dihydrate, R.G. | 0.2 mgs. | 5.0 gms. |
| Water for injection, USP q.s. add | 2.0 ml. | 50.0 liters |

*Includes a 5% manufacturing overcharge.

Procedure: For a 50.0 liter batch

Charge approximately 35 liters of water for injection to a suitable stainless steel jacketed vessel and heat to about 70°C. Charge the methylparaben and propylparaben to the heated water for injection and dissolve with agitation. When the parabens are completely dissolved, cool the contents of the tank to 25°–30°C by circulating cold water through the tank jacket. Sparge the solution with nitrogen gas for at least 10 minutes and keep covered with nitrogen during subsequent processing. Charge and dissolve the disodium EDTA and sodium bisulfite. Charge and dissolve the Antibiotic G-52 sulfate. Bring the batch volume up to 50.0 liters with water for injection and agitate until homogenous.

Under sterile conditions, filter the solution through a suitable bacteria retentive filter collecting the filtrate in a filling tank.

Fill the produce aseptically into sterile pyrogen free multiple dose vials, stopper and seal.

EXAMPLE 7

Antibiotic Ointment

| Antibiotic G-52 base | 10 gms. |
|---|---|
| Petrolatum | 990 gms. |

Procedure
1. Melt the petrolatum.
2. Admix Antibiotic G-52 base with about 10% of the molten petrolatum.
3. Pass the antibiotic - petrolatum mixture through a colloid mill.
4. Add in the remainder of the petrolatum and cool the mixture until it becomes semi-solid. At this stage the product may be put into suitable containers.

EXAMPLE 8

| Hard Gelatin Capsules | 10 mg. Capsule | 25 mg. Capsule | 100 mg. Capsule |
|---|---|---|---|
| Antibiotic G-52 (sulfate) | 10.50 mg.* | 26.25 mg.* | 105.00 mg.* |
| Lactose, Impalpable Powder | 238.50 mg. | 222.75 mg. | 144.00 mg. |
| Magnesium Stearate | 1.00 mg. | 1.00 mg. | 1.00 mg. |

*Based on 100% potency, plus 5% manufacturing overcharge.

Mix the lactose and the Antibiotic G-52 in a suitably-sized mixing vessel. Pass the mix through a mill, return to the mixing vessel and mix again. Pre-mix the magnesium stearate with a portion of the lactose-antibiotic mixture then blend into the entire batch. Fill into empty gelatin capsules using suitable encapsulating equipment.

We claim:

1. A composition of matter selected from the group consisting of Antibiotic G-52, non-toxic acid addition salts and Schiff base-oxazolidine derivatives thereof.

2. A composition of matter defined in claim 1, said composition of matter being Antibiotic G-52 having:

a. a molecular weight of 461 as determined by mass spectometry;

b. a pKa of 8.2;

c. the empirical formula $C_{20}H_{39}N_5O_7$;

d. a specific optical rotation as measured by D line of sodium of 156.4° in water at 0.3% concentration;

e. a nuclear magnetic resonance spectrum in deuterium oxide substantially as shown in FIG. 1;

f. an infrared absorption spectrum in mineral oil substantially as shown in FIG. 2; and said Antibiotic G-52 having the following structural formula:

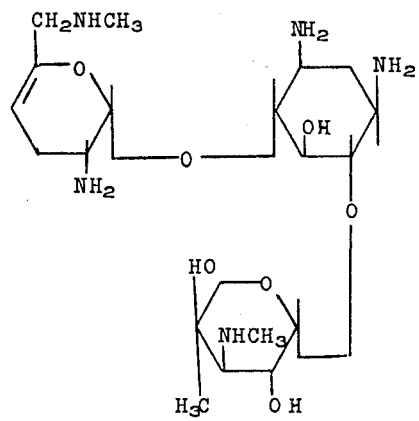

3. A composition of matter defined in claim 1, said composition being a non-toxic acid addition salt of Antibiotic G-52.

4. A composition of matter defined in claim 3, said compound being Antibiotic G-52 sulfate.

5. A Schiff base-oxazolidine derivative of Antibiotic G-52.

* * * * *